(12) United States Patent
Jean et al.

(10) Patent No.: US 10,746,645 B2
(45) Date of Patent: Aug. 18, 2020

(54) METHOD AND SYSTEM FOR PREDICTING ENGINE PERFORMANCE

(71) Applicant: PRATT & WHITNEY CANADA CORP., Longueuil (CA)

(72) Inventors: Maurice Jean, Boucherville (CA); Frederic Busnel, Montreal (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 256 days.

(21) Appl. No.: 15/884,804

(22) Filed: Jan. 31, 2018

(65) Prior Publication Data

US 2019/0234860 A1  Aug. 1, 2019

(51) Int. Cl.
| | |
|---|---|
| *G01N 15/10* | (2006.01) |
| *G01N 33/28* | (2006.01) |
| *G01M 15/14* | (2006.01) |
| *F01M 11/10* | (2006.01) |
| *F02D 41/14* | (2006.01) |
| *G01N 15/02* | (2006.01) |

(Continued)

(52) U.S. Cl.
CPC .............. *G01N 15/10* (2013.01); *F01M 11/10* (2013.01); *F02C 9/00* (2013.01); *F02D 41/1401* (2013.01); *G01M 15/14* (2013.01); *G01N 15/0227* (2013.01); *G01N 33/2888* (2013.01); *F02D 2041/1412* (2013.01); *F05D 2260/80* (2013.01); *F05D 2260/82* (2013.01); *F05D 2270/44* (2013.01); *G01N 15/0205* (2013.01); *G01N 2015/0053* (2013.01); *G01N 2015/0294* (2013.01); *G01N 2015/1087* (2013.01); *G01N 2015/1093* (2013.01); *G01N 2015/1493* (2013.01); *G01N 2015/1497* (2013.01)

(58) Field of Classification Search
CPC ................. F01M 11/10; F02D 41/1401; F02D 2041/1412; G01M 15/14; G01N 2015/1087; G01N 2015/1093; G01N 33/2888; F02C 9/00; F05D 2260/80; F05D 2260/82; F05D 2270/44
See application file for complete search history.

(56) References Cited

U.S. PATENT DOCUMENTS

| | | |
|---|---|---|
| 3,981,584 A | 9/1976 | Guymer |
| 5,210,704 A | 5/1993 | Husseiny |

(Continued)

*Primary Examiner* — Elias Desta
(74) *Attorney, Agent, or Firm* — Norton Rose Fulbright Canada LLP

(57) ABSTRACT

Systems and methods for predicting engine performance are provided herein. A fluid sample having particles suspended therein is received from a first engine. A plurality of particles are extracted from the fluid sample. Features of the plurality of particles extracted from the fluid sample and features of particles of reference fluid samples from a plurality of reference engines are obtained. A plurality of correlation indices indicative of a level of correlation between the first engine and each one of the plurality of reference engines is determined. The correlation indices are compared to a threshold to determine a subset of the plurality of reference engines. Performance history for the engines in the subset is obtained. From the performance history, the first engine is determined as having a similarity in performance with the engines in the subset. An output is generated indicating a predicted performance for the first engine.

20 Claims, 11 Drawing Sheets

(51) Int. Cl.
*F02C 9/00* (2006.01)
*G01N 15/00* (2006.01)
*G01N 15/14* (2006.01)

(56) References Cited

U.S. PATENT DOCUMENTS

| | | |
|---|---|---|
| 5,517,427 A | 5/1996 | Joyce |
| 5,572,320 A | 11/1996 | Reintjes et al. |
| 7,152,560 B2 * | 12/2006 | Miyanoo .................. F01L 1/34 123/90.15 |
| 9,562,484 B2 * | 2/2017 | Huang ................ F02D 41/0007 |
| 10,192,172 B2 * | 1/2019 | Chan ..................... G06F 16/248 |
| 2005/0114088 A1 | 5/2005 | Gorden et al. |
| 2014/0121994 A1 | 5/2014 | Jean et al. |
| 2016/0370341 A1 | 12/2016 | Jean et al. |
| 2017/0307583 A1 | 10/2017 | Jean |

\* cited by examiner

METHOD AND SYSTEM FOR PREDICTING ENGINE PERFORMANCE

TECHNICAL FIELD

The present disclosure relates generally to determining a similarity in performance between an engine and a plurality of reference engines, and, more particularly, to predicting engine performance based on the similarity in performance.

BACKGROUND OF THE ART

The analysis of engine oil or other lubricant for the purpose of identifying premature component wear has been performed for several decades using optical atomic spectroscopy (e.g., atomic emission spectroscopy (AES), as well as atomic absorption spectroscopy (AAS)). This technology was the basis for the military aviation's Spectroscopic Oil Analysis Program (SOAP). However, optical atomic spectroscopy has certain disadvantages, such as a lack of repeatability among different equipment and an inability to analyze particles greater than 5 μm in diameter. Furthermore, optical atomic spectroscopy is an elemental analysis of the total oil sample and typically does not characterize individual particles in the sample.

While there are existing techniques for fluid analysis from engines, there is still a need for methods and systems for predicting engine performance.

SUMMARY

There is described herein methods and systems for predicting engine performance for an engine, such as an aircraft engine, from a plurality of reference engines, such as reference aircraft engines. The methods and systems described herein utilize a technique for sample comparison referred to as a zoning and profiling approach.

In one aspect, there is provided a method for predicting engine performance. The method comprises receiving a fluid sample from a first engine, the fluid sample having particles suspended therein. The method comprises extracting a plurality of particles from the fluid sample. The method comprises obtaining features of the plurality of particles extracted from the fluid sample and obtaining the features of particles of reference fluid samples from a plurality of reference engines, the features comprising chemical composition and one or more physical characteristics of each particle. The method comprises determining, from the features, a plurality of correlation indices indicative of a level of correlation between the first engine and each one of the plurality of reference engines. The method comprises comparing the correlation indices to a threshold to determine a subset of the plurality of reference engines for which the threshold is exceeded. The method comprises obtaining performance history for the engines in the subset. The method comprises determining, from the performance history, that the first engine has a similarity in performance with the engines in the subset. The method comprises generating, based on the similarity in performance, an output indicating a predicted performance for the first engine.

In another aspect, there is provided a system for predicting engine performance. The system comprises one or more devices for receiving a fluid sample from a first engine, the fluid sample having particles suspended therein and extracting a plurality of particles from the fluid sample. The system comprises a non-transitory computer-readable memory having stored thereon program instructions executable by the at least one processing unit for: obtaining features of the plurality of particles extracted from the fluid sample and obtaining the features of particles of reference fluid samples from a plurality of reference engines, the features comprising chemical composition and one or more physical characteristics of each particle; determining, from the features, a plurality of correlation indices indicative of a level of correlation between the first engine and each one of the plurality of reference engines; comparing the correlation indices to a threshold to determine a subset of the plurality of reference engines for which the threshold is exceeded; obtaining performance history for the engines in the subset; determining, from the performance history, that the first engine has a similarity in performance with the engines in the subset; and generating, based on the similarity in performance, an output indicating a predicted performance for the first engine.

In another aspect, there is provided a computer readable medium having stored thereon program code executable by a processor for predicting engine performance, the program code comprising instructions for implementing the method for predicting an engine performance.

DESCRIPTION OF THE DRAWINGS

Reference is now made to the accompanying figures in which.

It will be noted that throughout the appended drawings, like features are identified by like reference numerals.

DETAILED DESCRIPTION

Figure 1:
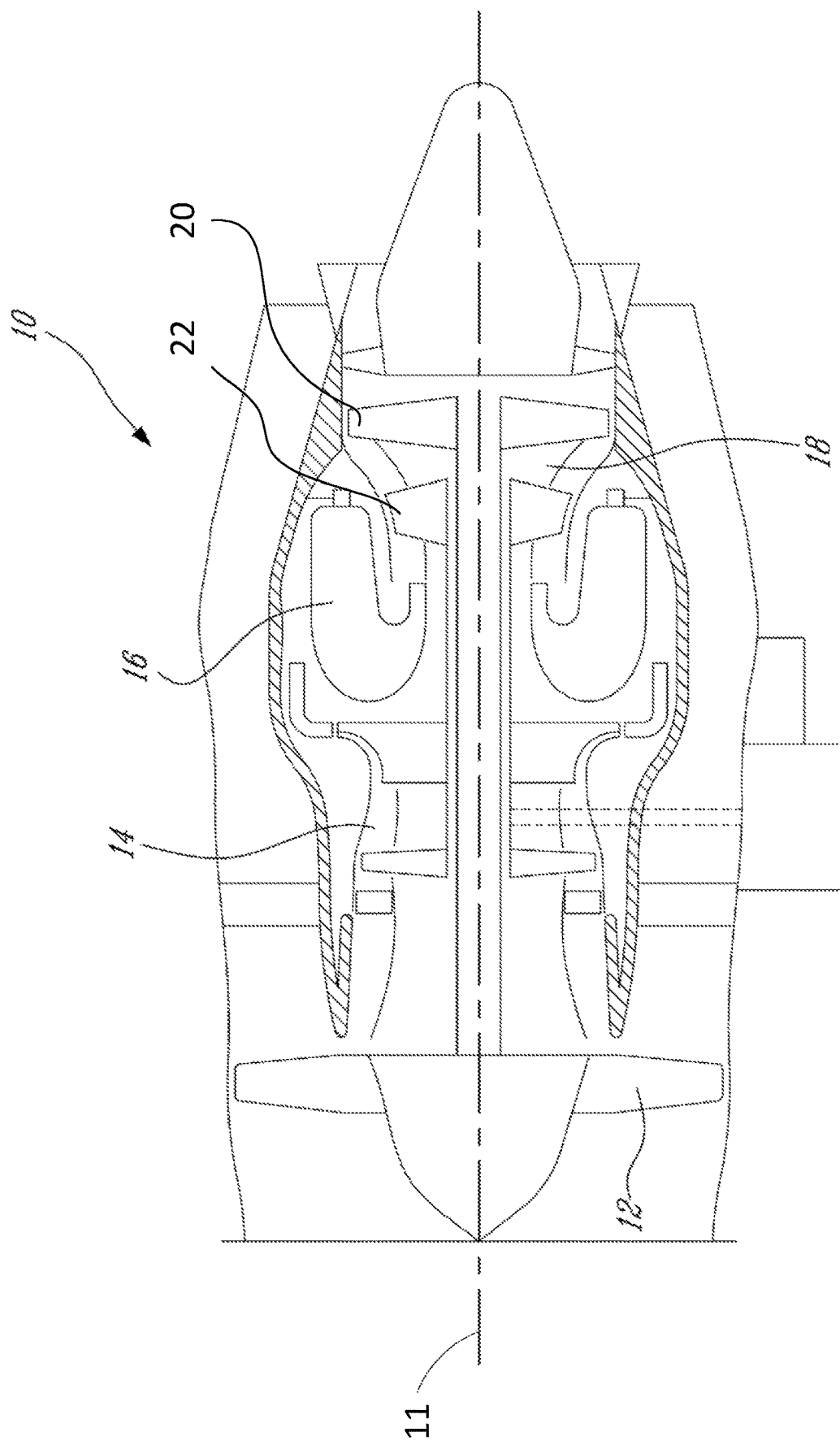
FIG. 1 is a schematic cross-sectional view of an example engine of an aircraft.

FIG. 1 illustrates a gas turbine engine 10 to which the methods and systems described herein may be applied. Note that while engine 10 is a turbofan engine, the methods and systems described herein may be applicable to turboprop, turboshaft, and other types engines. Engine 10 generally comprises in serial flow communication: a fan 12 through which ambient air is propelled, a compressor section 14 for pressurizing the air, a combustor 16 in which the compressed air is mixed with fuel and ignited for generating an annular stream of hot combustion gases, and a turbine section 18 for extracting energy from the combustion gases. Axis 11 defines an axial direction of the engine 10. In some embodiments, a low pressure spool is composed of a low pressure shaft and a low pressure turbine 20. The low pressure shaft drives the fan 12. A high pressure spool is composed of a high pressure turbine 22 attached to a high pressure shaft, which is connected to the compressor section 14.

Figure 2A:
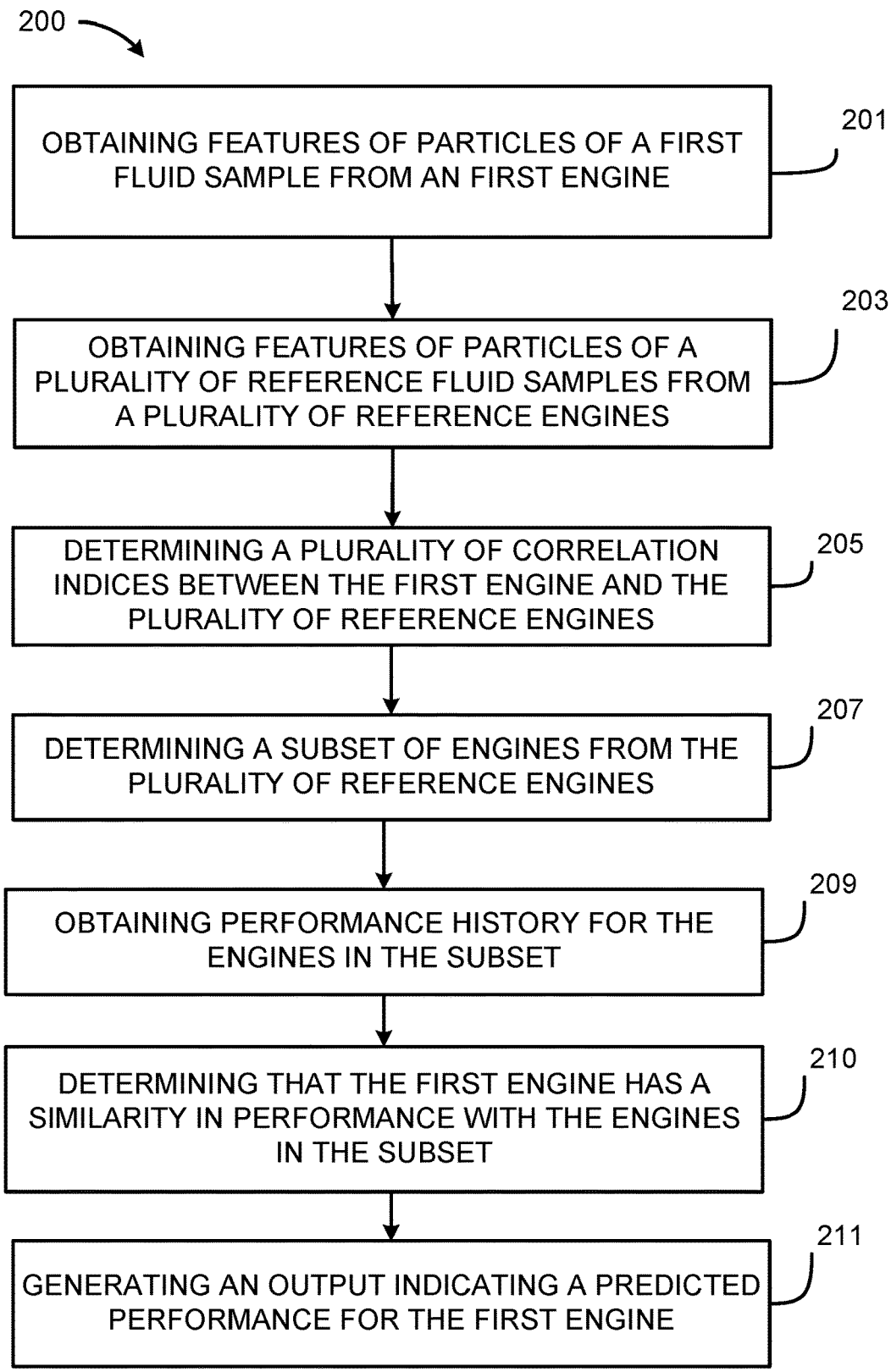
FIG. 2A is a flowchart illustrating an example method for predicting engine performance in accordance with an embodiment.

With reference to FIG. 2A, there is shown a flowchart illustrating an example method 200 for predicting engine performance of an engine, such as the engine 10 of FIG. 1. While the method 200 is described herein with reference to the engine 10 of FIG. 1, it should be understood that the method 200 may be applied to other types of engines depending on practical implementations.

In some embodiments, parts of the method 200 may be performed using aspects described by co-owned United States patent applications bearing publication Nos. 2014/0121994 and 2016/0370341 and U.S. patent application Ser. No. 15/884,561, the contents of which are hereby incorporated by reference.

At step 201, features (also referred to herein as parameters) of particles of a fluid sample from the engine 10 are obtained. The features of particles relate to a data representation of the particles. The features include, but are not limited to, one or more physical characteristics (e.g., size, aspect ratio and/or any other suitable physical characteristics) and chemical composition. Size refers to the longest dimension of a particle (i.e., maximum diameter). Aspect ratio refers to the longest dimension of a particle divided by the smallest dimension of the particle (i.e., a ratio of the longest dimension and the smallest dimension). In some embodiments, obtaining the features of the particles of the fluid sample from the engine 10 includes obtaining one or more profiles having particles identified from the fluid sample based one or more physical characteristics and chemical composition.

In accordance with an embodiment, each profile of particles is determined from a plurality of particles of a fluid sample based on a chemical composition of each particle satisfying a chemical composition criteria and based on physical characteristics (e.g., size and aspect ratio) of each particle satisfying a profile criteria. The process of determining a profile of particles based on each particle satisfying a chemical composition criteria and physical characteristics (e.g., size and aspect ratio) of each particle satisfying a profile criteria is referred to herein as a zoning and profiling approach. The process of identifying particles satisfying the chemical composition criteria is referred to herein as zoning. In other words, zoning refers to using chemical composition criteria to select particles from which a profile is ultimately established. The term "zone" may be used to refer to the particles that satisfy the chemical composition criteria. The process of characterizing particles using size and aspect ratio is referred to herein as profiling.

In accordance with a specific and non-limiting example of implementation, the profile has particles identified from the fluid sample based on size, aspect ratio and chemical composition.

In accordance with an embodiment, the features of particles are determined by receiving the fluid sample having particles suspended therein from the engine 10, extracting a plurality of particles from the fluid sample, and obtaining the features of the plurality of particles extracted from the fluid sample by identifying particles based on one or more physical characteristics and chemical composition.

At step 203, features of particles of a plurality of reference fluid samples is obtained. In accordance with an embodiment, each one of the plurality of reference fluid samples is from a respective one of a plurality of reference engines. In some embodiments, one or more of the plurality of reference fluid samples is from a same reference engine but taken a different time. For example, a reference fluid sample may be taken from the same reference engine after different run time durations (e.g., 0 hours, 50 hours, 100 hours, and/or any other suitable value). At step 203, the features of particles of the plurality of reference fluid samples may be obtained in a similar manner as the features of particles of the fluid sample at step 201. For example, one or more reference profiles having particles may be identified from a given reference fluid sample based one or more physical characteristics and chemical composition. The fluid sample at step 201 may be referred to as a "first fluid sample" to differentiate from the "reference fluid samples" of step 203. For similar reasons, the engine 10 referred to at step 201 may be referred to as a "first engine" to differentiate from the "reference engines".

In accordance with an embodiment, each one of the reference engines has a performance history associated therewith. For example, the performance history may be indicative of performance of a given reference engine without performance issues (e.g., without engine failure, without failure of a given engine component, or the like). By way of another example, the performance history may be indicative of performance of a given reference engine with performance issues. The performance issues may correspond to a condition of one or more components of a given engine, a failure of a given engine, a failure of a given component of a given engine, a predicted mechanism of failure, or any other suitable engine condition. Examples of predicted mechanism of failure include excess vibration, bearing wear, external contamination following engine maintenance, bearing rubbing, gear degradation, bearing cage and race degradation, among others. The performance history may include a negative performance indicator, such as a condition of one or more components of a given engine, a failure of a given engine, a failure of a given component of a given engine, a predicted mechanism of failure. The performance history may include a positive performance indicator of the engine such as a non-abnormal condition of a given engine or a non-abnormal condition of one or more components of a given engine or a given engine. In some embodiments, the chemical composition criteria may be determined based on a known failure mechanism. Accordingly, a given reference engine having known performance issue(s), and as such the features of the particles of the given reference engine may be used as a reference to predict if the first engine is likely to have the same performance issues as the given reference engine.

In some embodiments, obtaining the features of the particles at step 203 may comprise obtaining the features from a database. In some embodiments, data representing a plurality of particles filtered from a given fluid sample is obtained from the database and processing is performed to determine the profile.

At step 205, a plurality of correlation indices indicative of a level of correlation between the first engine and each one of the plurality of reference engines is determined. In accordance with an embodiment, the plurality of correlation indices are determined from the features. In accordance with an embodiment, each one of the correlation indices is determined based on the features of particles of the first fluid sample and the features of particles of a respective one of the plurality of reference fluid samples.

The determination of each correlation index may vary depending on practical implementations. For example, where a plurality of profiles is obtained for the first fluid sample and for each of the reference fluid samples, the correlation index may be determined differently from when a single profile is used. Similarly, when a plurality of zones are used, the correlation index may be determined differently from when a single zone is used.

In accordance with a specific and non-limiting example, each correlation index may be determined between the first engine and a given reference engine based on size and aspect ratio of identified particles of the first fluid sample and a corresponding reference engine fluid sample. In this example, each correlation index represents a correlation between a distribution of particles in both first fluid sample and a given reference engine fluid sample as a function of size and aspect ratio of the particles of the first fluid sample and the given reference engine fluid sample.

With reference to Table 1, a specific and non-limiting example of a plurality of correlation indices between the first engine and a plurality of reference engines is shown for a plurality of reference engines. As further shown, in this example, each one of the plurality of reference engines has a corresponding engine database number and a corresponding reference engine type. The engine database number is any suitable number used to identify a given reference engine and/or a given reference fluid sample. The reference engine type is any suitable number used to identify the engine make and/or model. In accordance with an embodiment, the first engine is of the same engine type as the plurality of reference engines.

TABLE 1

Correlation indices for a plurality of reference engines

| Reference Engine Type | Engine Database Number | Correlation Index |
|---|---|---|
| ZP0050 | ZP10 | 0.92 |
| ZP0050 | ZP11 | 0.75 |
| ZP0050 | ZP12 | 0.30 |
| ZP0050 | ZP13 | 0.45 |
| ZP0050 | ZP14 | 0.91 |
| ZP0050 | ZP15 | 0.99 |
| ZP0050 | ZP16 | 0.93 |
| ZP0050 | ZP17 | 0.40 |
| ZP0050 | ZP18 | 0.30 |
| ZP0050 | ZP19 | 0.05 |
| ZP0050 | ZP20 | 0.09 |
| ZP0050 | ZP21 | 0.30 |
| ZP0050 | ZP22 | 0.40 |

At step 207, a subset of engines from the plurality of reference engines is determined based on the plurality of correlation indices. In accordance with an embodiment, each one of the plurality of correlation indices is compared to a threshold to determine the subset of the plurality of reference engines. For example, the subset of the plurality of reference engines may comprise each reference engine having a correlation index exceeding the threshold. The threshold may vary depending on practical implementation. For example the threshold may be 0.95 (or 95%), 0.9 (or 90%), 0.85 (or 85%), or any other suitable value. The threshold may be determined based on the chemical composition criteria and/or the profile criteria. The threshold may vary from one reference engine to another. The threshold may be determined based on performance history and/or performance issues of a given reference engine.

In some embodiments, the plurality of reference engines are ranked according to the correlation indices and a selected number of the highest ranking reference engines is chosen as the subset of engines.

At step 209, the performance history for each engine in the subset of the plurality of reference engines is obtained. In some embodiments, obtaining the engine performance history comprises obtaining a number of performance issues for each engine in the subset of the plurality of reference engines. The number of performance issues for each engine in the subset of the plurality of reference engines may be the number of performance issues that occur after a predetermined run time. For example, the predetermined run time may be 500 hours and/or any other suitable value. In some embodiments, the number of performance issues corresponds to a count of the number of component failures of an engine and/or predicted mechanism of failure. In some embodiments, the number of performance issues corresponds to a count of the number of times maintenance and/or repair was performed on a given engine. Other manners of classifying the number of performance issues may vary depending on practical implementations.

In some embodiments, the engine database number is used to obtain the number of performance issues. For example, Table 2 illustrates a specific and non-limiting example of table correlating the engine database number with the number of performance issues associated with each one of the reference engines.

TABLE 2

Number of performance issues

| Engine Database Number | Number of Performance Issues |
|---|---|
| ZP10 | 3 |
| ZP11 | 2 |
| ZP12 | 0 |
| ZP13 | 0 |
| ZP14 | 2 |
| ZP15 | 0 |
| ZP16 | 1 |
| ZP17 | 0 |
| ZP18 | 0 |
| ZP19 | 0 |
| ZP20 | 2 |
| ZP21 | 0 |
| ZP22 | 2 |

Table 3 shows a specific and non-limiting example of a table identifying a subset of engines from the plurality of reference engines of Table 1 with the corresponding number of performance issues from Table 2. As shown, the data in Table 1 is sorted according to the value of each correlation index for exceeding a threshold. In this example, the threshold to determine the subset of the plurality of reference engines is 0.9 and the engines with database numbers ZP15, ZP10, ZP16 and ZP14, which are respectively associated with correlation indices of 0.99, 0.92, 0.93, and 0.91, are included in the subset of engines. The number of performance issues of each reference engine from Table 2 is also shown.

TABLE 3

Identification of a subset of engines from the plurality of reference engines

| Reference Engine Type | Engine Database Number | Correlation Index | Number of Performance Issues |
|---|---|---|---|
| ZP0050 | ZP15 | 0.99 | 0 |
| ZP0050 | ZP10 | 0.92 | 3 |
| ZP0050 | ZP16 | 0.93 | 1 |
| ZP0050 | ZP14 | 0.91 | 2 |

At step 210, from the performance history, the first engine is determined to have a similarly in performance with the engines in the subset of reference engines. In some embodiments, the similarity in performance comprises determining a likelihood that the first engine will have a performance history similar to that of one or more engines in the subset. In some embodiments, an average number of performance issues is determined and a likelihood that the first engine will have performance issues is determined based on the average number of performance issues. For instance, in the specific and non-limiting example of Table 3, the average number of performance issues would be determined as (0+3+1+2)/4=1.5, which may then be used to determine the likelihood that the first engine will have performance issues. By way of a specific and non-limiting example, if the average number of performance issues is between 0 and 1, this may indicate a low chance of the first engine having performance issues; if the average number of performance issues is between 1 and 3, this may indicate a moderate chance of the first engine having performance issues; if the average number of performance issues is above 3, this may indicate a high chance of the first engine having performance issues. The ranges for predicting if the first engine has a low, moderate or high chance of having performance issues may vary depending on practical implementation. Similarly, the classifications of low, moderate or high may vary to have more or less than three classes.

In some embodiments, the determined similarity in performance may be used to indicate that further tests and/or inspection should be performed on the first engine in order to improve its reliability.

In some embodiments, the first engine is a production engine that has been produced and not yet put into use (e.g., on an aircraft). In such a case, the predicted similarity in performance may indicate that the production engine may have the performance history of one or more of the engines in the subset of the plurality of reference engines.

In accordance with an embodiment, at step 211, an output is generated indicating a predicted performance for the first engine. The output is generated based on the determined similarity in performance. In accordance with an embodiment, the output indicates that the first engine has a likelihood of having the performance history of one or more of the engines in the subset. The output may include the performance history of one or more of the engine in the subset. The output may include the number of performance issues and/or the average number of performance issues. The output may indicate the negative performance indicator or the positive performance indicator. The output may indicate when the engine is expected to fail, the mechanism of failure of the engine and/or any other suitable information. In some embodiments, the output may include an indicator to monitor the first engine.

In some embodiments, monitoring of the first engine may be done on regular or irregular intervals according to method 200. For example, month-to-month monitoring of the first engine may be done according to method 200. The monitoring may be for trend monitoring purposes. For example, the monitoring may be done to satisfy, at least in part, the ARP5758 standard for "Trend Analysis for Maintaining Correlation of Gas Turbine Engine Test Cells". It should be appreciated that many monitoring approaches are based on the knowledge of critical performance indicators and acceptable values, which, in one embodiment, the approach of method 200 does not require knowledge thereof.

Figure 2B:
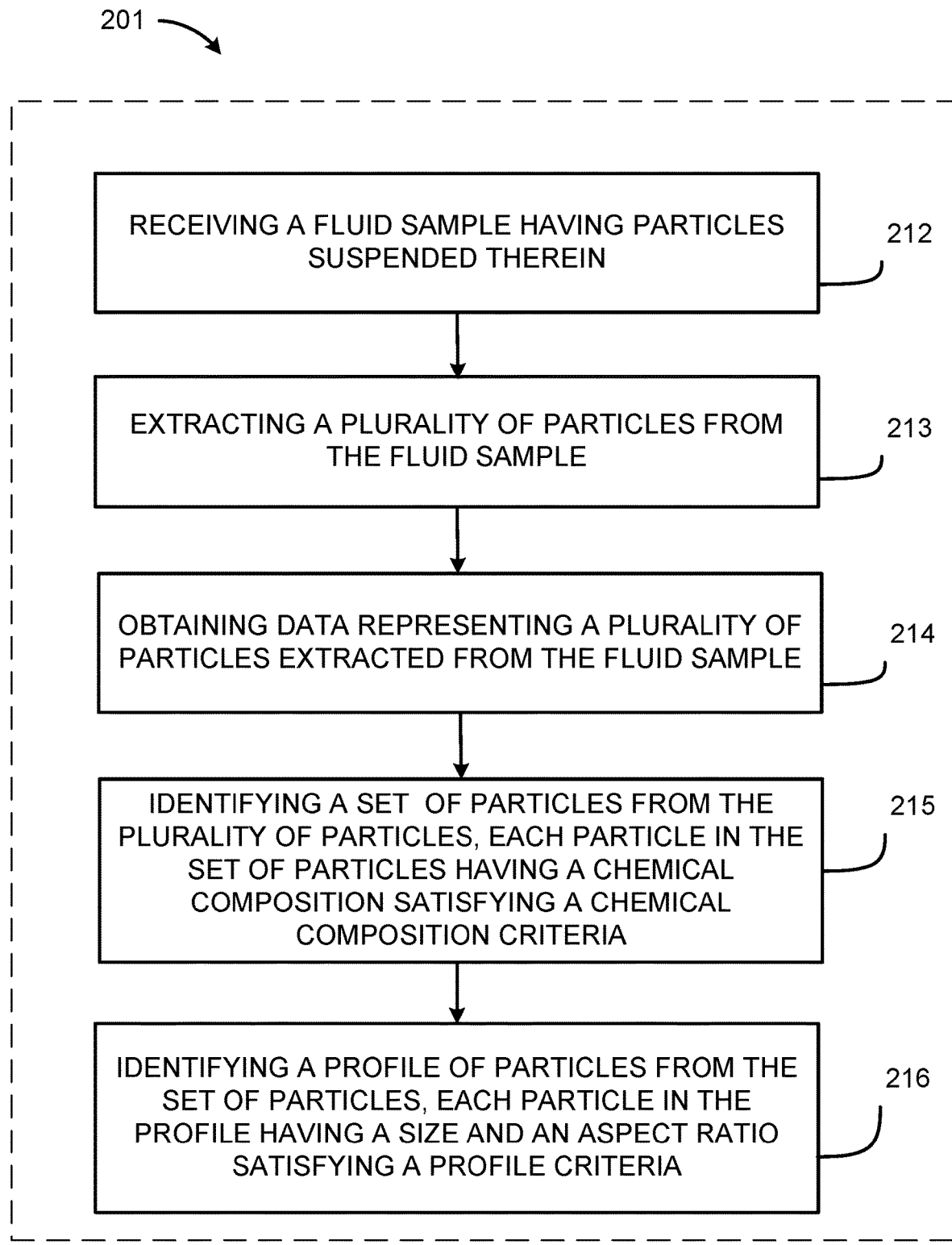
FIG. 2B is a flowchart illustrating an example method for obtaining a profile of particles by zoning and profiling in accordance with an embodiment.

With additional reference to FIG. 2B, a flowchart illustrates an example of obtaining features of particles of a fluid sample in accordance with an embodiment of step 201. In other words, FIG. 2B illustrates an example embodiment of zoning and profiling. At step 212, the fluid sample having particles suspended therein is received from the engine 10. The fluid sample may be an oil or other lubricant sample removed from the engine 10. In the example of an oil sample from an aircraft engine, the oil sample may be collected by the aircraft operator. In some examples, more than one sample may be obtained from the engine 10. A relatively small amount of oil (e.g., 25 mL or less) may be sufficient. The amount of oil sample obtained may be selected in order to obtain a certain number of particles suspended therein. For example, it may be known or expected that a given engine should have a certain concentration of particles in the oil after a certain number of operating hours. The volume of oil sample obtained may thus be determined in order to obtain a minimum quantity of particles. The frequency of sampling may be determined based on the flight hours per year, the maturity of the engine, the typical behavior of the engine type and/or the history of unscheduled engine removal for that engine type, for example. The sample may be obtained and prepared using any suitable method.

At step 213, a plurality of particles are extracted from the fluid sample removed from the engine 10. The particles are extracted from the fluid sample using any suitable method. In accordance with an embodiment, particles extracted are relatively small particles that are not typically captured by conventional engine oil filters. Indeed, an engine oil filter typically only filters large particles and/or an oil plug of an engine typically only has large particles stuck thereon. It should be appreciated that, by using relatively small particles for analysis according to methods and/or systems described herein, a more accurate prediction of an engine condition may ultimately be obtained as large particles may not provide an accurate time indicator of a condition of the engine. Furthermore, removing debris from an engine oil filter is usually costly as the engine oil filter typically cannot be reused. Moreover, removing an engine oil filter may be time consuming.

In some embodiments, a collected oil sample may be filtered using a very fine filter, such as a 0.22 μm filter, in order to filter out particles of a given size (e.g., particles having a diameter of 0.22 μm or more). The particles obtained may range in size from about 0.22 μm to about 1600 μm, for example, although particles of other sizes may also be obtained. The volume of oil sample filtered and the size of the sample prepared may vary, such as according to the number of particles in the oil. The volume of oil sample that is filtered may be determined based on the type of engine and/or the expected normal levels of particles in the oil.

In some embodiments, the extracted particles are cleaned to remove any residue (e.g., oil). For example, a solvent may be used to clean the particles. Any other suitable technique for cleaning the particles may be used At step 214, data representing a plurality of particles extracted from the fluid sample is obtained. In accordance with an embodiment, raw data representing a plurality of features of each of the plurality of particles filtered from the fluid sample is collected at step 214. Each particle is analyzed to determine a plurality of features, such as one or more physical characteristics (e.g., aspect ratio and size) and/or chemical composition (e.g., alloy type and chemical composition). In accordance with an embodiment, an x-ray spectroscopy device comprising one or more emitters and one or more detectors is used for this analysis. A scanning electron microscope (SEM) equipped to perform x-ray spectroscopy may be used for this analysis, although any other suitable methods may also be used. In accordance with an embodiment, the SEM produces images of the particles by scanning the particles with a focused beam of electrons. In accordance with an embodiment, the SEM comprises one or more emitters for emitting the beam of electrons. The emitted electrons interact with atoms of the particles, producing signals that contain information about the particles' surface topography and/or composition. In accordance with an embodiment, SEM comprises one or more detectors for collecting electronics (e.g., secondary electrons emitted by atoms excited by the electron beam). The signals collected by the collected electrons may be processed to produce signals that contain information about the sample's surface topography and/or composition. In accordance with an embodiment, an X-Ray Fluorescence (XRF) device is used for carrying out particles analysis. XRF is a non-destructive analytical technique used to determine the elemental composition of materials. In accordance with an embodiment, the XRF device comprises one or more emitters for emitting x-rays and one or more detectors for measuring the fluorescent (or secondary) x-ray emitted from the particles when they are excited by the one or more emitters. The XRF device may process the measured fluorescent x-ray and determine the chemical composition of the particles. In some embodiments, the SEM may be coupled to an X-Ray Fluorescence (XRF) detector and/or device for carrying out particle analysis. For example, an automated SEM may be used. Software and/or hardware in the system may automatically recognize the presence of a particle and may then automatically move a stage and an electron beam on the particle to perform the particle analysis. The particle chemical composition, size and/or aspect ratio may also be determined automatically. Any other suitable equipment may be used to perform this analysis.

Suitable image analyzer software, such as those conventionally used with SEM, may be used to collect data about particle physical characteristics and/or chemical composition. Analysis of each particle may produce a respective set of data for that particle, for example there may be up to 70 data points for each particle, the data describing various features of the particle (e.g., size, aspect ratio and chemical composition, among others).

The data obtained from this analysis may be further processed, in order to account for any measurement error and/or the possible presence of contamination. This further processing may be carried out by categorizing the particles as described below, where each particle is categorized based on the determined features (e.g., physical characteristics and/or chemical composition).

It should be appreciated that the conventional SOAP technique typically relies on elemental analysis using emission/atomic absorption analysis of particles. The particles analyzed are typically limited to 2-3 µm or smaller. The result of SOAP is typically a quantification of elements (e.g., iron) by volume (e.g., in ppm), without a consideration of the physical characteristics and the chemical composition of the particle, and may produce a relatively small number of data points (e.g., about 30 data points that describe the total quantities of individual elements in the total sample). In accordance with an embodiment of the present disclosure, the zoning and profiling approach considers physical characteristics and chemical composition of each individual particle, rather than overall characteristics of the total sample.

At step 215, a set of particles is identified from the plurality of particles, where each particle in the set of particles has a chemical composition satisfying a chemical composition criteria. Each particle may be categorized based on chemical composition and the plurality of particles may be identified from the categorization of each particle according to the chemical composition criteria. Categorization of particles may be based on, for example, the absolute chemical composition. Categories may be defined according to different alloy compositions, association with one specific manufacturing process and/or association with one particular source (e.g., engine component), for example. Categories may also be defined by the elemental composition or single material of the particles. By way of example, each particle may be categorized according to a percentage of each element (e.g., a particle may be categorized as 17.5% chromium, 7.5% nickel and 75% iron). The chemical composition criteria, for example, may be particles within respective ranges (i.e., lower and upper limits) of a percentage of each element (e.g., 10 to 20% chromium, 5 to 10% nickel, and 70 to 85% iron). In other words, in some embodiments, a chemical composition of a given particle satisfies the chemical composition criteria when a concentration range of at least one element of the given particle is within lower and upper limits that vary as a function of a given element. The chemical composition criteria when defined as one or more concentration ranges of a given particle may be referred to as a specific zone. In some embodiments, the chemical composition criteria is selected so as to ensure that the range of an element is large enough to contain a certain quantity of particles and small enough to limit to one type of material.

By way of another example, particles may be classified in a category such as "Environmental", "Metallic", "Non-metallic", "Plating", or "Miscellaneous", among others. Each particle may be further categorized into sub-category levels. As an example, the "Metallic" category may have a level 1 sub-category of "Copper", within which may be level 2 sub-categories of "Bronze" and "Brass". In some examples, five levels of decision may be used to categorize each particle into a specific level (e.g., metallic, copper, bronze, leaded bronze or machining chip). The chemical composition criteria may be one or more categories (e.g., the "Metallic" category with a sub-category of "Copper").

Categories may be defined according to a level of interaction and/or an interaction zone as described by co-owned United States patent application bearing publication No. 2016/0370341. For example, particles may be identified that fall within the interaction zone. The interaction zone may correspond to a concentration range for at least a first element found in a first material and at least a second element found in at least a second material, the concentration range may be defined by upper and lower limits that vary as a function of a given element, the upper limit may correspond to a minimum concentration for the given element in one of the first material and the second material, and the lower limit may correspond to a maximum concentration for the given element in the other of the first material and the second material. It should be appreciated that two parts made of different materials may generate debris that will be a mix of both materials and by measuring the mixture may help in identifying a failure involving these two parts.

In some embodiments, zones are determined based on the engine type, make and/or model. In accordance with a specific and non-limiting example, for Pratt & Witney PW127 engine, specification of the material used to produce bearing, gear, cage, silver plating, may be used as a zone.

At step 216, the profile of particles is identified from the set of particles, where each particle in the profile of particles has a size and aspect ratio satisfying a profile criteria. For example, the size and the aspect ratio of a given particle may satisfy the profile criteria when the size of the given particle is within lower and upper size limits and the aspect ratio of the given particle is within lower and upper aspect ratio limits. The lower and upper size limits and the lower and upper aspect ratio limits may be set according to percentiles of the size and aspect ratio of the particles in the set of particles. In other words, the lower size limit may be a lower percentile limit of the size of the particles in the set of particles, the upper size limit may be an upper percentile limit of the size of the particles in the set of particles, the lower aspect ratio limit may be a lower percentile limit of the aspect ratio of the particles in the set of particles and the upper aspect ratio limit may be an upper percentile limit of the aspect ratio of the particles in the set of particles. For example, the profile of particles may be identified from the set of particles based on each particle in the profile of particles having a size within a 20 to 80 percentile of the sizes of the particles of the set of particles and having an aspect ratio within a 20 to 80 percentile of the aspect ratios of the particles of the set of particles. By way of another example, the lower and upper size limits and the lower and upper aspect ratio limits may be numerical value limits (e.g., a size between 0.8 µm and 2.8 µm and an aspect ratio between 1.2 and 2.4). The lower and upper size limits and the lower and upper aspect ratio limits may vary depending on practical implementations.

The process of the flowchart of FIG. 2B may be used for obtaining features of particles of a fluid sample in accordance with an embodiment of step 203. In other words, the steps 212 to 216 of FIG. 2B may be used to determine a given reference profile of particles. For example, in some embodiments, for each one of the plurality of reference fluid samples a reference set of particles of a respective reference fluid sample is determined, where each particle in the reference set of particles has a chemical composition satisfying the chemical composition criteria. In some embodiments, for each one of the plurality of reference fluid samples, a reference profile of particles from the reference set of particle is determined, where each particle in the reference profile has a size and an aspect ratio satisfying a profile criteria. In accordance with an embodiment, the chemical composition criteria and/or the profile criteria at step 203 is the same as described at step 201.

Figure 3A:
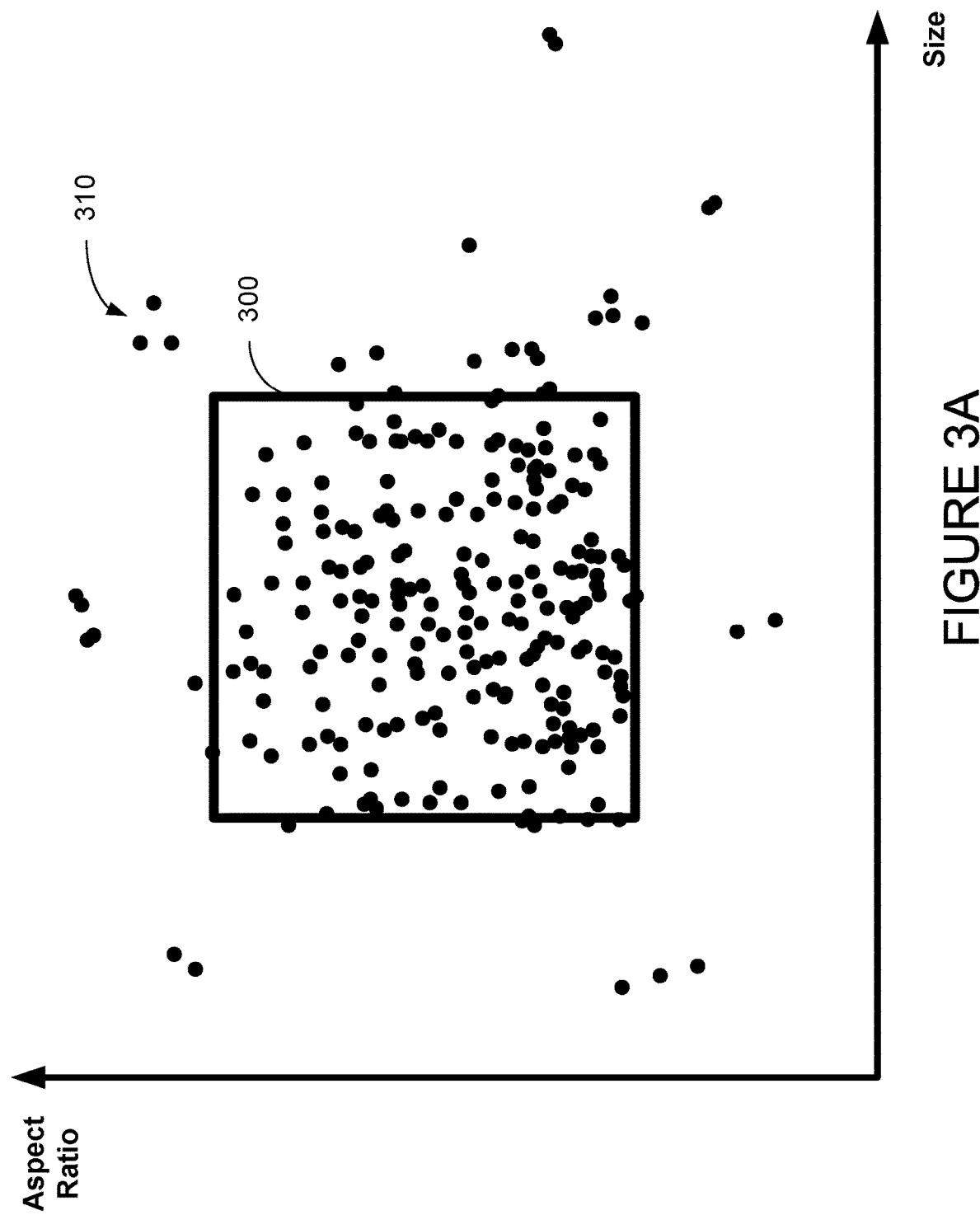
FIG. 3A is a graphical representation of a first profile of particles in accordance with an embodiment.

With reference to FIG. 3A, an example of a first profile 300 of particles and a first set 310 of particles is shown. In this example, each particle in a first set 310 satisfies the chemical composition criteria. The particles in the first profile 300 is a subset of particles from the first set 310, where each particle in the first profile 300 satisfies the profile criteria. With additional reference to FIG. 3B, an example of a reference profile 400 of particles and a second set 410 of particles is shown in combination with the first profile 300 and the first set 310. In this example, the reference profile 400 is illustrated of a profile of one of the plurality of reference fluid samples. For the purposes of illustrative clarity, the particles in the first set 310 are represented by solid circles and the particles in the second set 410 are represented by unfilled circles. In this example, each particle in the second set 410 satisfies the chemical composition criteria. The particles in the reference profile 400 are a subset of particles from the second set 310, where each particle in the reference profile 400 satisfies the profile criteria. As illustrated, the first profile 300 has a center 320 and the reference profile 410 has a center 420. In accordance with an embodiment, the center of a profile is defined as the $50^{th}$ percentile for size and the $50^{th}$ percentile for aspect ratio of the particles in a given profile. In this example, the center 320 is the $50^{th}$ percentile for size and the $50^{th}$ percentile for aspect ratio of the particles in the first profile 300. Similarly, in this example, the center 420 is the $50^{th}$ percentile for size and the $50^{th}$ percentile for aspect ratio of the particles in the reference profile 400.

Figure 2C:
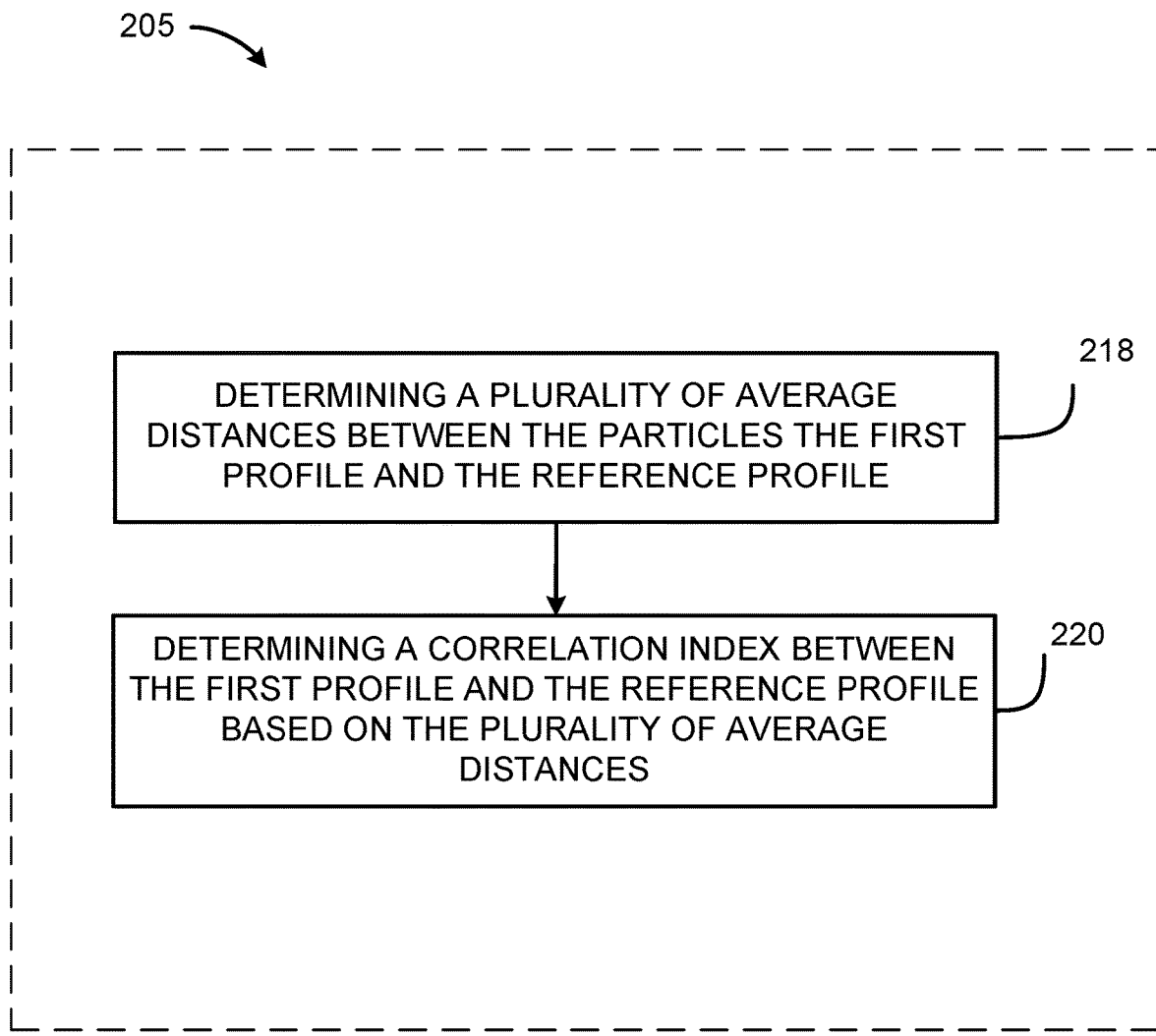
FIG. 2C is a flowchart illustrating an example method for determining a correlation index between particles in a first profile and a reference profile in accordance with an embodiment.
Figure 3B:
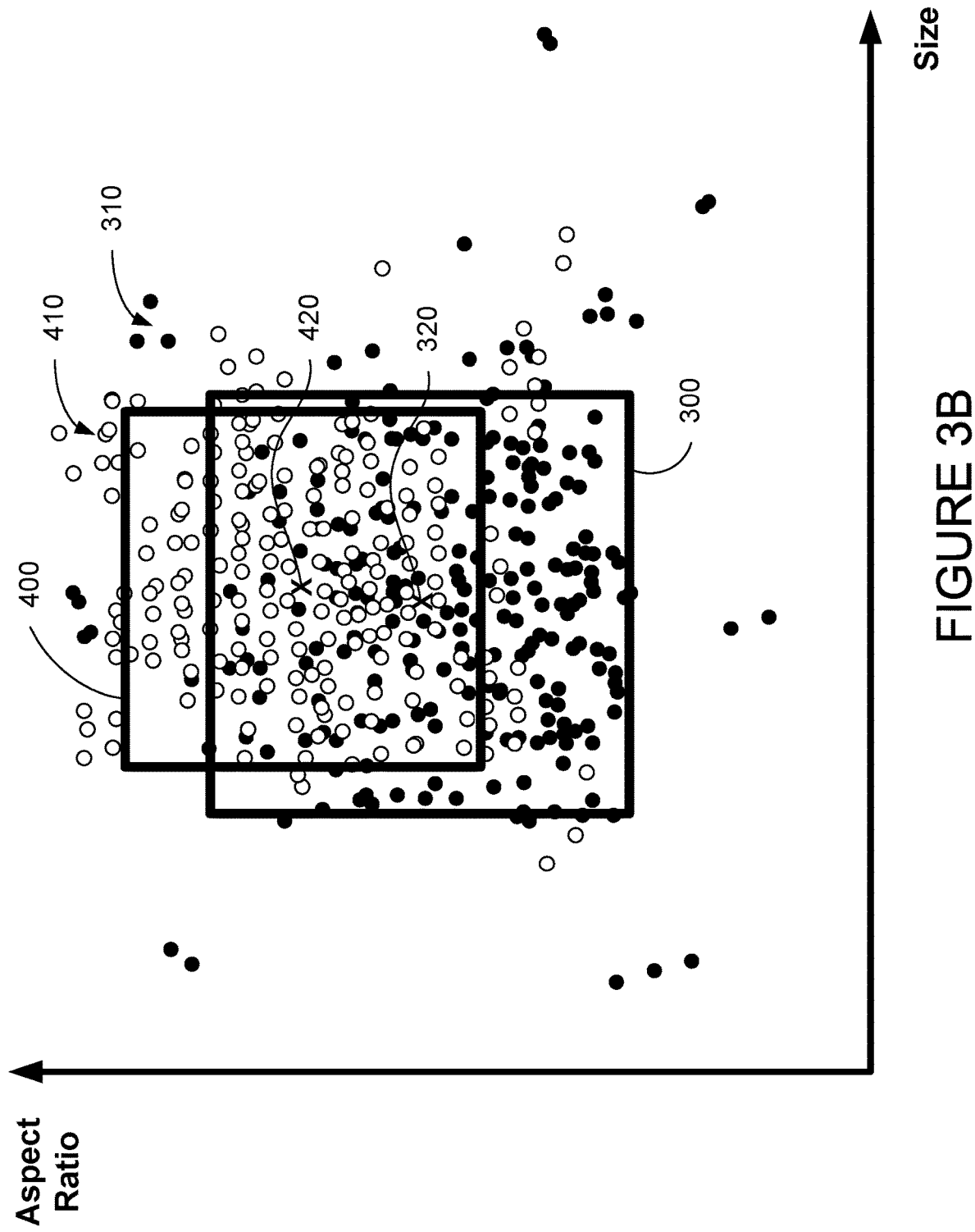
FIG. 3B is a graphical representation of the first profile of particles and a second profile of particles in accordance with an embodiment.

With additional reference to FIG. 2C, a flowchart illustrates an example of determining the correlation index between the particles in the first profile 300 and the reference profile 400 in accordance with an embodiment of step 205. At step 218, a plurality of average distances is determined between particles in each of the first profile 300 and the reference profile 400 and a respective center 320, 420 of each of the first profile 300 and the reference profile 400. In accordance with an embodiment, the plurality of average distances is determined using size and aspect ratio as axes of a two-dimensional coordinate system used to position particles in a two-dimensional Euclidean space. For example, a first axis of the coordinate system may correspond to size and a second axis of the coordinate system may correspond to aspect ratio (e.g., as shown in FIGS. 3A and 3B). At step 220, the correlation index is determined based on the plurality of average distances.

The process illustrated in FIG. 2C may be performed for each one of the plurality of reference fluid samples to determine the plurality of correlation indices. Accordingly, for each one of the plurality of reference fluid samples, a plurality of average distances between particles in each of the first profile and the reference profile and a respective center of each of the first profile and the reference profile is determined. A correlation index may be determined based on the respective plurality of average distances, for each one of the plurality of reference fluid samples.

Figure 2D:
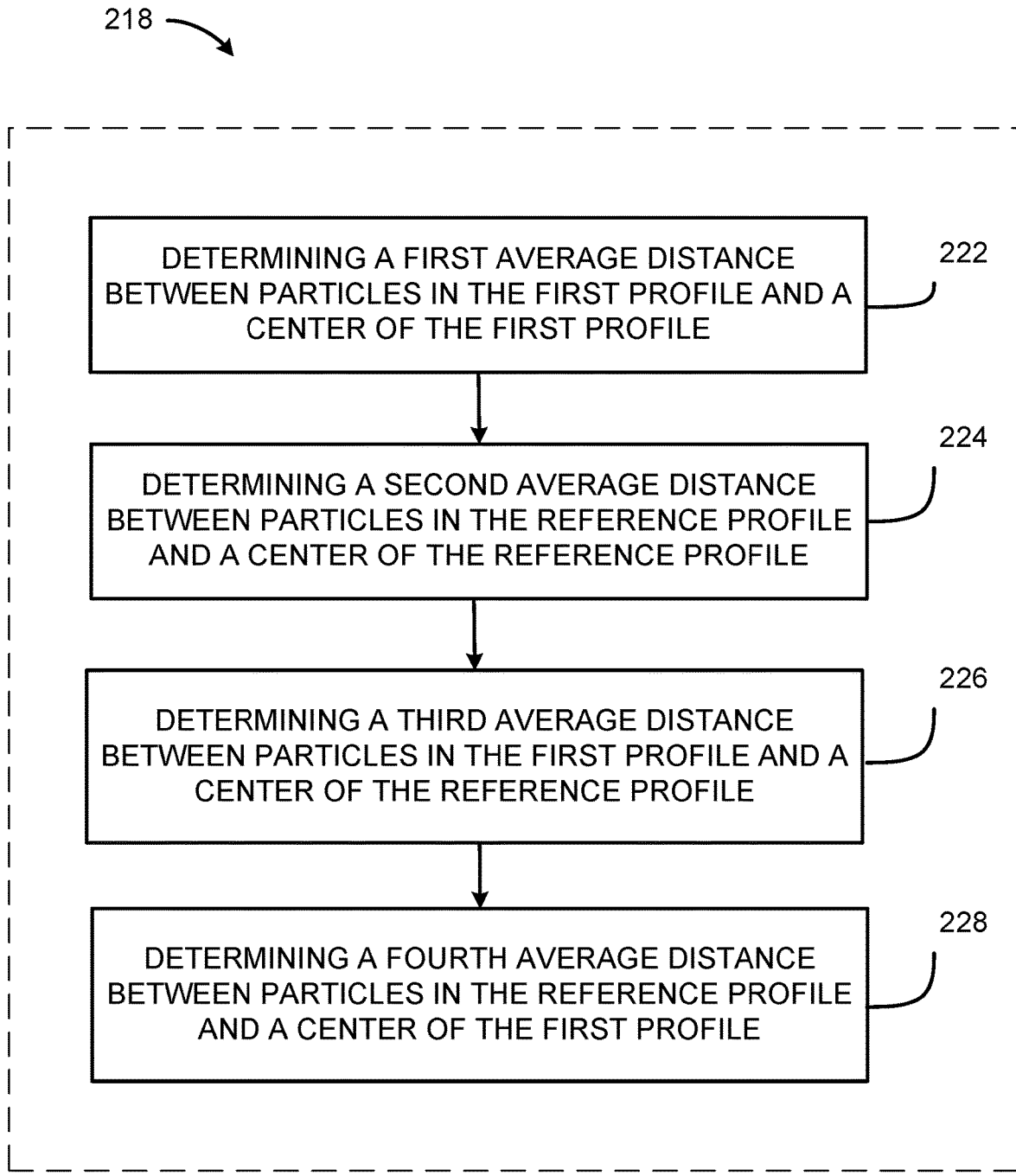
FIG. 2D is a flowchart illustrating an example method for determining a plurality of average distances between particles in each of a first profile and a reference profile in relation to a center of each of the first profile and the reference profile in accordance with an embodiment.

With additional reference to FIG. 2D, a flowchart illustrates an example of determining the plurality of average distances between the first profile 300 and the reference profile 400 in accordance with an embodiment of step 218 of FIG. 2C. At step 222, a first average distance between particles in the first profile 300 and the center 320 of the first profile 300 is determined.

The average distance may be referred to as an average mathematical distance (AMD). The AMD for a profile k is the square of the average distances between particles in the profile k and the mathematical center of profile k. The AMD for the profile k may be represented by equation (1):

$$AMD_{k,k} = \frac{\sum_{i}^{Nb_k} \left(\sqrt{Size_{k_i}} - \sqrt{Size_{MC_k}}\right)^2 + \left(\sqrt{Ratio_{k_i}} - \sqrt{Ratio_{MC_k}}\right)^2}{Nb_k}, \quad (1).$$

The subscript k.k indicates that the AMD has been calculated for particles in the profile k using the mathematical center of profile k. $Nb_k$ refers to the number of particles in the profile k. $size_{k_i}$ refers to the size of the i-th particle in profile k and $Ratio_{k_i}$ refers to the aspect ratio of the i-th particle in profile k. $size_{MC_k}$ refers to the $50^{th}$ percentile for size and $Ratio_{MC_k}$ refers to the $50^{th}$ percentile for aspect ratio for the particles in the profile k.

In accordance with an embodiment, the first average distance between particles in the first profile 300 and the center 320 of the first profile 300 is determined according to equation (1). The first average distance may be represented by $AMD_{1,1}$.

At step 224, a second average distance between particles in the reference profile 400 and the center 420 of the reference profile 400 is determined. The center of the reference profile 400 may be defined as the $50^{th}$ percentile for size and the $50^{th}$ percentile for aspect ratio of particles in the reference profile. Similar to step 222, the second average distance between particles in the reference profile 400 and the center 420 of the reference profile 400 may be determined according to equation (1). The second average distance may be represented by $AMD_{2,2}$.

At step 226, a third average distance between particles in the first profile 300 and the center 420 of the reference profile 400 is determined. The AMD for the profile k with the mathematical center of profile j is the square of the average distances between particles in the profile k and the mathematical center of profile j and may be represented by equation (2):

$$AMD_{k,j} = \frac{\sum_{i}^{Nb_k} \left(\sqrt{Size_{k_i}} - \sqrt{Size_{MC_j}}\right)^2 + \left(\sqrt{Ratio_{k_i}} - \sqrt{Ratio_{MC_j}}\right)^2}{Nb_k}, \quad (2).$$

The subscript k.j indicates that the AMD has been calculated for particles in the profile k using the mathematical center of profile j. $Nb_k$ refers to the number of particles in the profile k. $size_{k_i}$ refers to the size of the i-th particle in profile k and $Ratio_{k_i}$ refers to the aspect ratio of the i-th particle in profile k. $size_{MC_j}$ refers to the $50^{th}$ percentile for size for profile j and $Ratio_{MC_j}$ refers to the $50^{th}$ percentile for aspect ratio for profile j.

In accordance with an embodiment, the third average distance between particles in the first profile 300 and the center 420 of the reference profile 400 is determined according to equation (2). The third average distance may be represented by $AMD_{1,2}$.

At step 228, a fourth average distance between particles in the reference profile 400 and the center 320 of the first profile 300 is determined. In a similar manner to that of step 224, the fourth average distance between particles in the reference profile 400 and the center 320 of the first profile 300 may be determined according to equation (2). The fourth average distance may be represented by $AMD_{2,1}$.

Figure 2E:
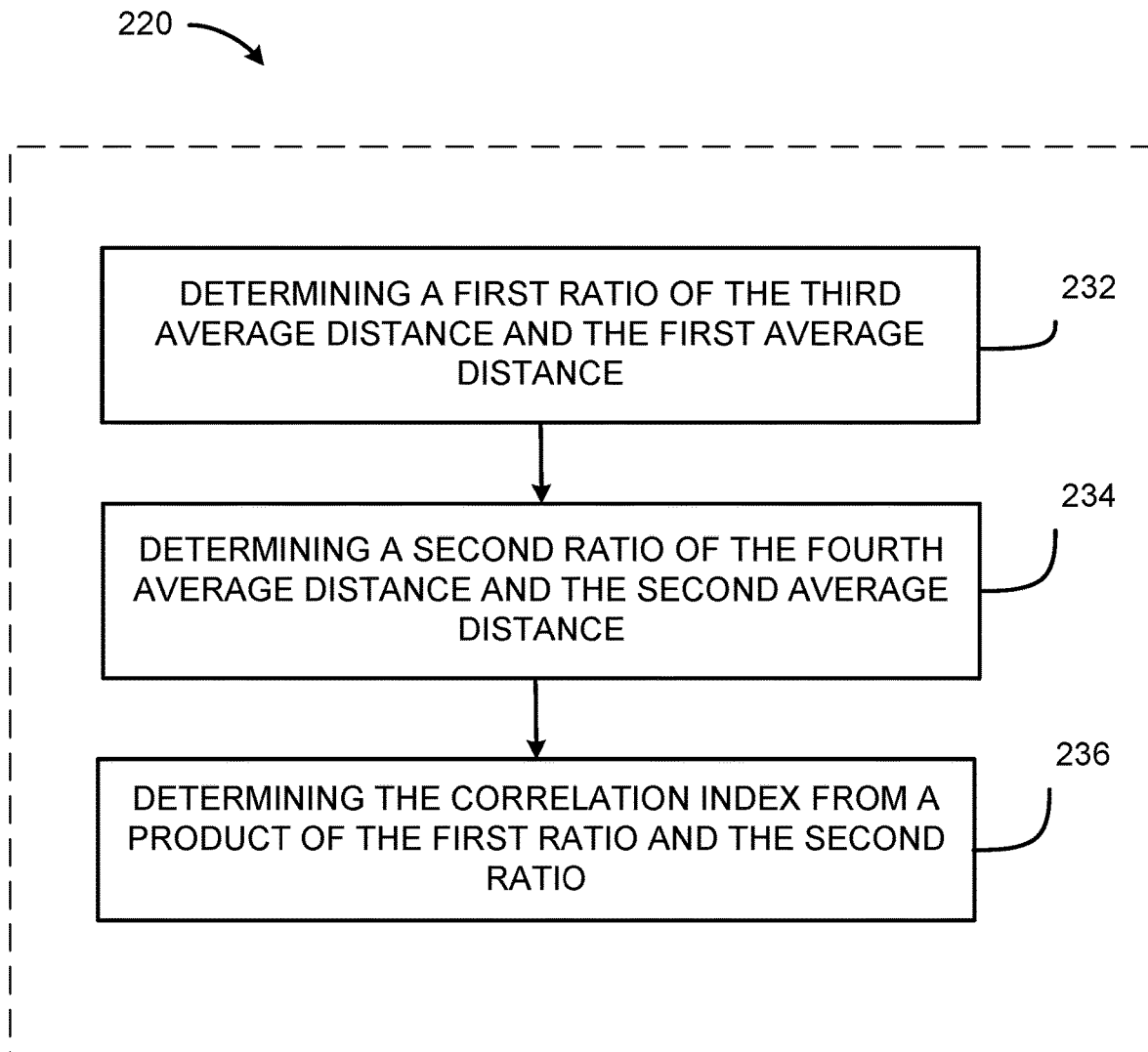
FIG. 2E is a flowchart illustrating an example method for determining a correlation index between particles in the first profile and reference profiles from the plurality of average distances determined according to FIG. 2D in accordance with an embodiment.

With additional reference to FIG. 2E, a flowchart illustrates an example of determining the correlation index from the first, second, third and fourth average distances in accordance with an embodiment of step 220 of FIG. 2C. At step 232, a first ratio of the third average distance and the first average distance is determined. The ratio may be represented by equation (3):

$$\frac{AMD_{k,j}}{AMD_{k,k}}, \quad (3)$$

Equation (3) signifies a difference in the distribution of profile k using the mathematical center of profile j. In accordance with an embodiment, this reference is smaller than one; if the $AMD_{k,j}$ is greater than $AMD_{j,k}$, then the reverse ratio may be used.

The first ratio may be represented as:

$$\frac{AMD_{1,2}}{AMD_{1,1}}$$

At step 234, a second ratio of the fourth average distance and the second average distance is determined. Similar to step 232, the second ratio may be determined according to equation (3). The second ratio may be represented as:

$$\frac{AMD_{2,1}}{AMD_{2,2}}$$

At step 236, the correlation index is computed as a product of the first and second ratios. The correlation index may be determined by equation (4):

$$CI_{j,k} = \frac{AMD_{k,j}}{AMD_{k,k}} \times \frac{AMD_{j,k}}{AMD_{j,j}}, \quad (4)$$

The correlation index for the first profile 300 and the reference profile 400 may be represented by:

$$CI_{1,2} = \frac{AMD_{1,2}}{AMD_{1,1}} \times \frac{AMD_{2,1}}{AMD_{2,2}}$$

If the correlation index is equal to 1 (or 100%) this is indicative of perfect correlation between the first profile 300 and the reference profile 400. The higher the correlation index, the higher a similarity between the first profile 300 and the reference profile 400. Thus, for example, the correlation index may be indicative of a similarity between the engine 10 and a given reference engine, when the chemical composition criteria and/or the profile criteria are designed to be indicative of an engine condition of the reference engine.

It should be appreciated that, in this example, the correlation index is indicative of the similarity between the first profile 300 and the reference profile 400.

In some embodiments, the first profile 300 may be represented by a first matrix and the reference profile 400 may be represented by a second matrix. One of the rows or columns of a given matrix may correspond to size and one of the rows or columns of the given matrix may correspond to aspect ratio. The matrix may be used to determine the correlation index.

Figure 2F:
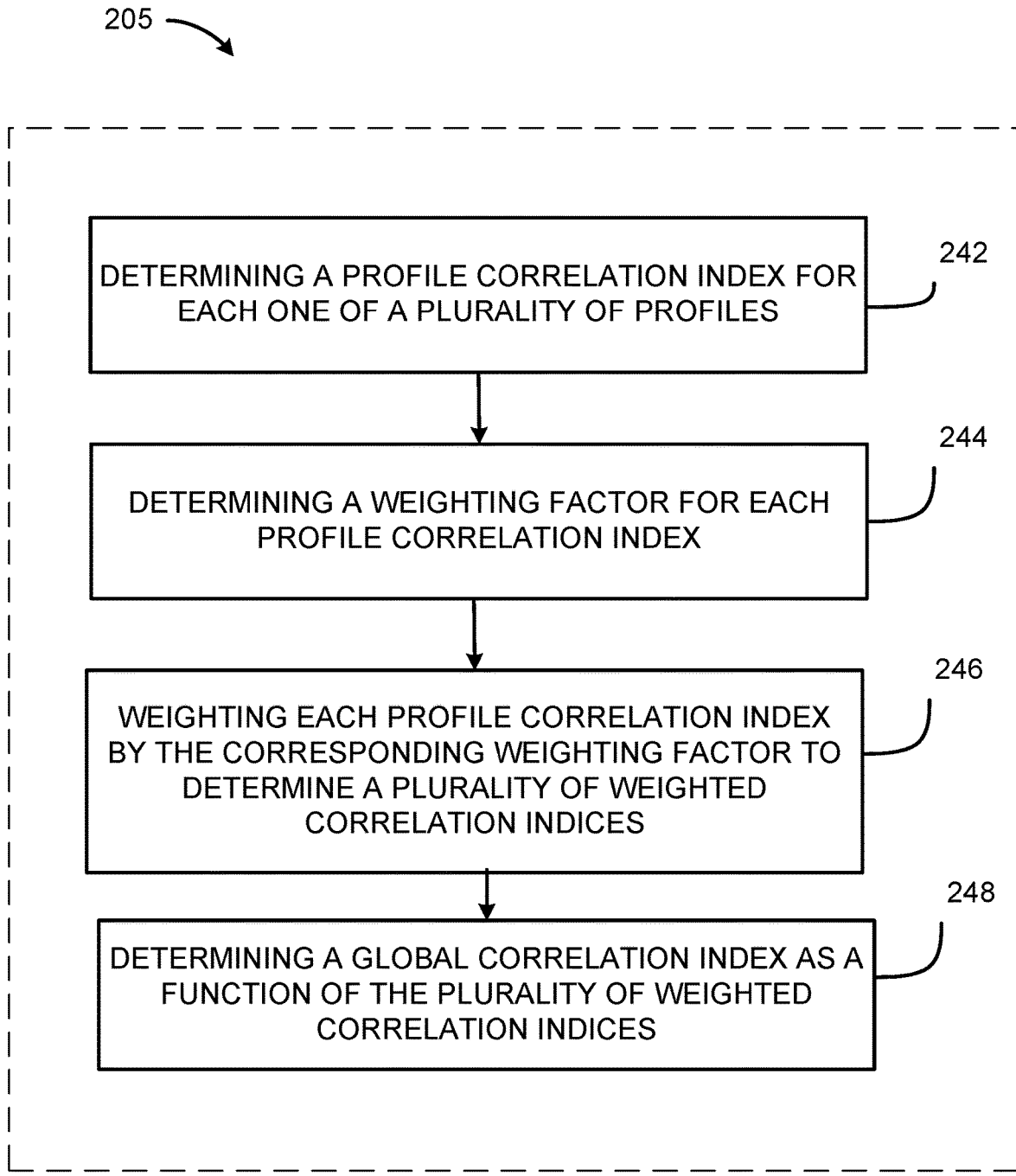
FIG. 2F is a flowchart illustrating an example method for determining a correlation index for a plurality of profiles in accordance with an embodiment.

In some embodiments, method 200 may be performed using a plurality of zones. In other words, a plurality of chemical composition criteria may be used to determine a plurality of profiles for the first fluid sample and a plurality of profiles for each one of the plurality of reference fluid samples. With reference to FIG. 2F, a flowchart illustrates an example of determining the correlation index when a plurality of profiles are utilized in accordance with an embodiment of step 205 of FIG. 2A. The steps of FIG. 2F may be performed for each one of the plurality of reference fluid samples to determine a global correlation index for each one of the plurality of reference fluid samples. At step 242, a profile correlation index is determined for each one of the plurality of profiles of the first fluid sample in relation to a corresponding reference profile. In other words, a set of profile correlation indices indicative of a level of correlation between a plurality of profiles of particles of the first fluid sample and a corresponding plurality of profiles of particles from a respective one of the plurality of reference fluid samples is determined. In accordance with an embodiment, each profile correlation index is determined based on average distances associated with a respective one of the plurality of sample profiles in relation to a corresponding reference profile of particles. For example, steps 222, 224, 226 and 228 of FIG. 2D may be performed for each one of the plurality of profiles of the first fluid sample in relation to a corresponding reference profile to determine a plurality of average distances for each one of the plurality of profiles. Similarly, steps 232, 234 and 236 of FIG. 2E may be performed for each one of the plurality of profiles and the result would be a plurality of profile correlation indices, each one associated with a respective profile of the plurality of profiles.

At step 244, a weighting factor for each profile correlation index is determined. In some embodiments, the weighting factor is determined based on a population of particles of a respective one of the plurality of profiles, because the number of particles (i.e., the population) in a given profile may vary. The weighting factor may be referred to as a population factor. The population factor for profile k and profile j may be referred to as $PF_{jk}$ and be represented by equation (5):

$$PF_{jk} = \frac{\log(NB_j + 1)}{\log(NB_k + 1)}, \quad (5)$$

$Nb_k$ refers to the number of particles in the profile k and $Nb_j$ refers to the number of particles in the profile j. The population factor may be determined for each one of the plurality of profiles of the first fluid sample in respect to a corresponding reference profile. In accordance with an embodiment, the population factor (PF) is a number equal to or less than 1. If $Nb_j$ is greater than $Nb_k$, the reverse of the ratio in equation (5) is used.

At step 246, a plurality of weighted correlation indices is determined based on weighting each profile correlation index by the corresponding weighting factor for each profile correlation index. For example, each profile correlation index may be multiplied by the corresponding population factor to determine the plurality of weighted correlation indices. If there are no particles in a given profile, the corresponding weighting factor for that profile may be set to 1 (or 100%).

At step 248, the global correlation index is determined as a function of the plurality of weighted correlation indices. For example, the global correlation index may be determined from a product of the plurality of weighted correlation indices. By way of another example, the global correlation index may be determined from the summation of the plurality of weighted correlation indices. The function for determining the global correlation index may vary depending on practical implementation and may comprise one or more of a product, summation, subtraction, division, and/or any other suitable arithmetic function or combination of functions. The global correlation index may then be used in step 205 of FIG. 2A as the correlation index between the first engine and a give reference engine.

The determination of the plurality of zones may vary. For example, one or more zones having a large number of particles (i.e. a number of particles greater than a predetermined threshold) may be chosen. By way of another example, one or more zones may be selected where the zones correspond with a failure mode. The selection of the zones may be validated by comparing similar and non-similar samples. Accordingly, the threshold value for determining that the global correlation index is indicative of two fluid samples being similar may be established for every type of zone and/or sample.

In some embodiments, at step 210 a comparison with several reference samples with specific conditions may be used to predict a failure mechanism. Accordingly, determining a similarity in performance between the first engine and the subset of engines may comprise generating a prediction of any possible future failure and/or failure mechanism. The generated prediction may be recorded and saved for further action and/or future reference. Using the generated prediction, appropriate action may be taken. In some embodiments, corrective action(s) (e.g., engine removal or increased frequency of testing) may be determined based on the prediction. In some examples, prediction of expected failure and/or failure mechanism may involve review by an expert, a technical specialist and/or an operator. Where failure of a particular part has been predicted, the part may be replaced and/or monitored with greater frequency. Alternatively, where failure of the engine has been predicted, the engine may be placed on a tighter maintenance and/or oil analysis schedule. For example, the disclosed methods may include performing a maintenance or pre-maintenance action on the engine. Maintenance or pre-maintenance actions that may be performed include, for example, flagging the engine for maintenance (e.g., in a maintenance file), generating a notification to alert a user for the need to perform maintenance, scheduling maintenance for the engine, and performing the appropriate maintenance, among others. The maintenance or pre-maintenance action performed may be dependent on the generated prediction.

Figure 4:
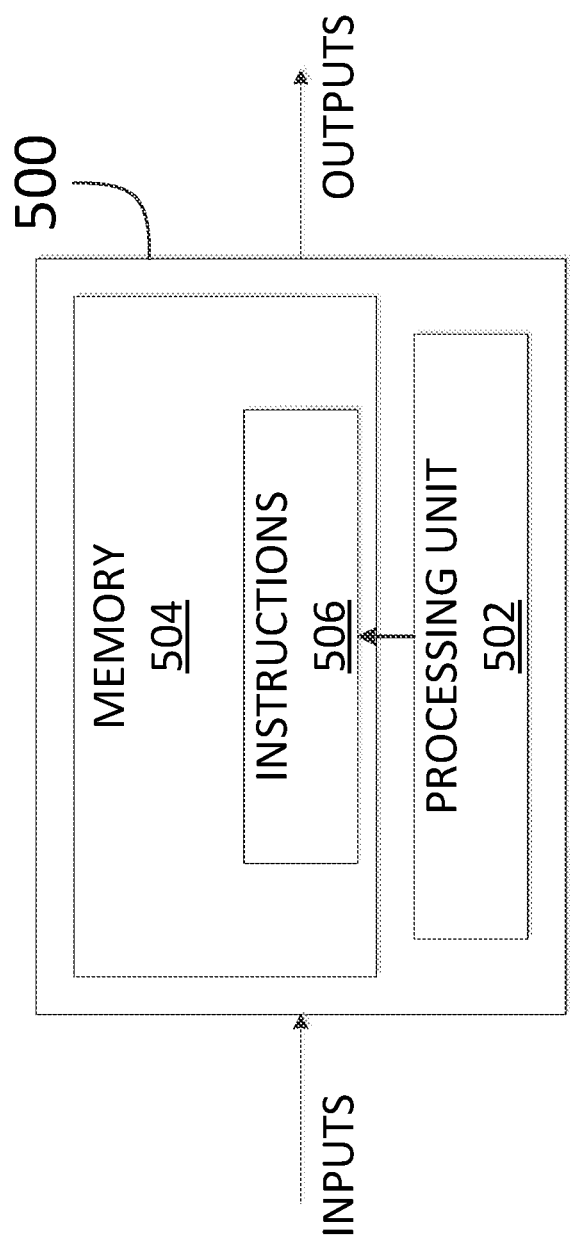
FIG. 4 is a block diagram of an example computing device for implementing the method of FIGS. 2A to 2F in accordance with an embodiment.

With reference to FIG. 4, the method 200 may be implemented by a computing device 500, comprising a processing unit 502 and a memory 504 which has stored therein computer-executable instructions 506. The processing unit 502 may comprise any suitable devices configured to implement the system such that instructions 506, when executed by the computing device 500 or other programmable apparatus, may cause the functions/acts/steps of the method 200 as described herein to be executed. The processing unit 502 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, or any combination thereof.

The memory 504 may comprise any suitable known or other machine-readable storage medium. The memory 504 may comprise non-transitory computer readable storage medium, for example, but not limited to, an electronic, magnetic, optical, electromagnetic, infrared, or semiconductor system, apparatus, or device, or any suitable combination of the foregoing. The memory 504 may include a suitable combination of any type of computer memory that is located either internally or externally to device, for example random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Memory 504 may comprise any storage means (e.g., devices) suitable for retrievably storing machine-readable instructions 506 executable by processing unit 502.

The methods and systems described herein may be implemented in a high level procedural or object oriented programming or scripting language, or a combination thereof, to communicate with or assist in the operation of a computer system, for example the computing device 500. Alternatively, the methods and systems may be implemented in assembly or machine language. The language may be a compiled or interpreted language. Program code for implementing the methods and systems may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems may also be considered to be implemented by way of a non-transitory computer-readable storage medium having a computer program stored thereon. The computer program may comprise computer-readable instructions which cause a computer, or in some embodiments the processing unit 502 of the computing device 500, to operate in a specific and predefined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

Figure 5:
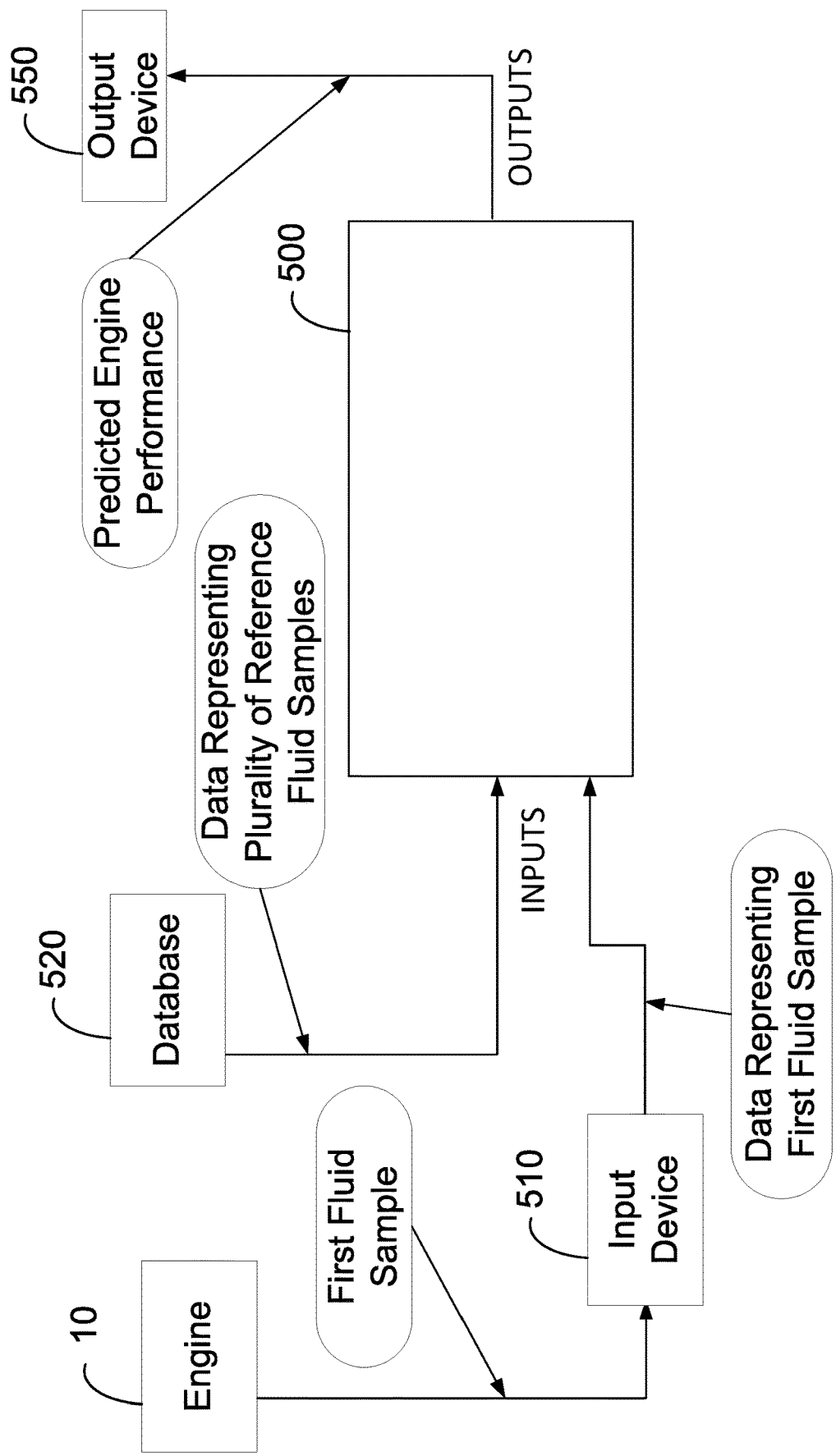
FIG. 5 is a block diagram of on an example computing system configured for predicting engine performance in accordance with an embodiment.

FIG. 5 illustrates a specific and non-limiting example of implementation of a system for predicting engine performance. In this example, a first fluid sample is taken from the engine 10 and the input device 510 processes the first fluid sample to obtain data representing the first fluid sample. The input device 510 may comprise one or more of the physical devices/systems described elsewhere in this document, such as SEM, XRF, etc. The data representing the first fluid sample is inputted into the computing device 500 from the input device 510. In this example, the computing device 500 obtains data representing the plurality of reference fluid samples from a database 520. The computing device 500 may perform the method 200 to generate an output indicating a predicted performance for the first engine. The computing device outputs the predicted performance to an output device 550 (e.g., a display device, printer, networked device or any other suitable output device).

While examples are described herein with reference to an aircraft engine, the method and system for determining a similarity in performance between a first engine and one or more reference engines described herein may be used with reference to other types of engines.

In some embodiments, the zoning and profiling approach may be used for quality assurance or for calibration of equipment.

It should be appreciated that the zoning and profiling approach may allow for a better comparison of one single test engine with other test engines with known performance issues. The comparison may take into consideration the fact that each failure mode may have its own characteristic profile.

It should further be appreciated that a particular engine type may be known to have certain failure patterns. Accordingly, the zoning and profiling approach may be used to determine that an engine has a likelihood of a failure pattern. It should further be appreciated that two or more engine types may share the same or similar mechanism of failure. Accordingly, the zoning and profiling approach may be used to determine a mechanism of failure.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure.

Various aspects of the methods and systems for predicting an engine condition may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be obvious to those skilled in the art that changes and modifications may be made without departing from this invention in its broader aspects. The scope of the following claims should not be limited by the embodiments set forth in the examples, but should be given the broadest reasonable interpretation consistent with the description as a whole.

What is claimed is:

1. A method for predicting engine performance, the method comprising:
   receiving a fluid sample from a first engine, the fluid sample having particles suspended therein;
   extracting a plurality of particles from the fluid sample;
   obtaining features of the plurality of particles extracted from the fluid sample and obtaining the features of particles of reference fluid samples from a plurality of reference engines, the features comprising chemical composition and one or more physical characteristics of each particle;
   determining, from the features, a plurality of correlation indices indicative of a level of correlation between the first engine and each one of the plurality of reference engines;

comparing the correlation indices to a threshold to determine a subset of the plurality of reference engines for which the threshold is exceeded;
obtaining performance history for the engines in the subset;
determining, from the performance history, that the first engine has a similarity in performance with the engines in the subset; and
generating, based on the similarity in performance, an output indicating a predicted performance for the first engine.

2. The method of claim 1, wherein obtaining the features of the plurality of particles extracted from the fluid sample comprises:
identifying a first set of particles of the fluid sample, each particle in the first set of particles having a chemical composition satisfying a chemical composition criteria; and
identifying a first profile of particles from the first set of particles, each particle in the first profile having a size and an aspect ratio satisfying a profile criteria.

3. The method of claim 2, wherein obtaining the features of particles of the plurality of reference fluid samples comprises:
for each one of the plurality of reference fluid samples:
identifying a reference set of particles of a respective reference fluid sample, each particle in the reference set of particles having a chemical composition satisfying the chemical composition criteria; and
identifying a reference profile of particles from the reference set of particles, each particle in the reference profile having a size and an aspect ratio satisfying a profile criteria.

4. The method of claim 3, wherein determining the plurality of correlation indices comprises:
for each one of the plurality of reference fluid samples:
determining, using size and aspect ratio as axes of a two-dimensional coordinate system, a plurality of average distances between particles in each of the first profile and the reference profile and a respective center of each of the first profile and the reference profile; and
determining a correlation index based on the plurality of average distances.

5. The method of claim 1, wherein determining the plurality of correlation indices comprises:
for each one of the plurality of reference fluid samples:
determining a set of profile correlation indices indicative of a level of correlation between a plurality of profiles of particles of the fluid sample and a plurality of profiles of particles from a respective one of the plurality of reference fluid samples;
determining a weighting factor for each one of the profile correlation indices;
weighting each one of the profile correlation indices by the weighting factor to determine a plurality of weighted correlation indices; and
determining a global correlation index as a function of the plurality of weighted correlation indices.

6. The method of claim 1, wherein obtaining the performance history for the engines in the subset comprises obtaining a number of performance issues for each engine in the subset.

7. The method of claim 6, wherein the number of performance issues for each engine in the subset is the number of performance issues after a predetermined run time.

8. The method of claim 6, wherein determining that the first engine has the similarity in performance with the engines in the subset comprises:
determining an average number of performance issues from the number of performance issues for each engine in the subset; and
determining a likelihood that the first engine will have performance issues based on the average number of performance issues.

9. A system for predicting engine performance, the system comprising:
one or more devices for:
receiving a fluid sample from a first engine, the fluid sample having particles suspended therein; and
extracting a plurality of particles from the fluid sample; and
at least one processing unit; and
a non-transitory computer-readable memory having stored thereon program instructions executable by the at least one processing unit for:
obtaining features of the plurality of particles extracted from the fluid sample and obtaining the features of particles of reference fluid samples from a plurality of reference engines, the features comprising chemical composition and one or more physical characteristics of each particle;
determining, from the features, a plurality of correlation indices indicative of a level of correlation between the first engine and each one of the plurality of reference engines;
comparing the correlation indices to a threshold to determine a subset of the plurality of reference engines for which the threshold is exceeded;
obtaining performance history for the engines in the subset;
determining, from the performance history, that the first engine has a similarity in performance with the engines in the subset; and
generating, based on the similarity in performance, an output indicating a predicted performance for the first engine.

10. The system of claim 9, wherein obtaining the features of the plurality of particles extracted from the fluid sample comprises:
identifying a first set of particles of the fluid sample, each particle in the first set of particles having a chemical composition satisfying a chemical composition criteria; and
identifying a first profile of particles from the first set of particles, each particle in the first profile having a size and an aspect ratio satisfying a profile criteria.

11. The system of claim 10, wherein obtaining the features of particles of the plurality of reference fluid samples comprises:
for each one of the plurality of reference fluid samples:
identifying a reference set of particles of a respective reference fluid sample, each particle in the reference set of particles having a chemical composition satisfying the chemical composition criteria; and
identifying a reference profile of particles from the reference set of particles, each particle in the reference profile having a size and an aspect ratio satisfying a profile criteria.

12. The system of claim 11, wherein determining the plurality of correlation indices comprises:

for each one of the plurality of reference fluid samples:
determining, using size and aspect ratio as axes of a two-dimensional coordinate system, a plurality of average distances between particles in each of the first profile and the reference profile and a respective center of each of the first profile and the reference profile; and
determining a correlation index based on the plurality of average distances.

13. The system of claim 9, wherein determining the plurality of correlation indices comprises:
for each one of the plurality of reference fluid samples:
determining a set of profile correlation indices indicative of a level of correlation between a plurality of profiles of particles of the fluid sample and a plurality of profiles of particles from a respective one of the plurality of reference fluid samples;
determining a weighting factor for each one of the profile correlation indices;
weighting each one of the profile correlation indices by the weighting factor to determine a plurality of weighted correlation indices; and
determining a global correlation index as a function of the plurality of weighted correlation indices.

14. The system of claim 9, wherein obtaining the performance history for the engines in the subset comprises obtaining a number of performance issues for each engine in the subset.

15. The system of claim 14, wherein the number of performance issues for each engine in the subset is the number of performance issues after a predetermined run time.

16. The system of claim 14, wherein determining that the first engine has the similarity in performance with the engines in the subset comprises:
determining an average number of performance issues from the number of performance issues for each engine in the subset; and
determining a likelihood that the first engine will have performance issues based on the average number of performance issues.

17. A computer readable medium having stored thereon program code executable by a processor for predicting engine performance, the program code comprising instructions for:
obtaining features of a plurality of particles extracted from a fluid sample from a first engine and obtaining the features of particles of reference fluid samples from a plurality of reference engines, the features comprising chemical composition and one or more physical characteristics of each particle;
determining, from the features, a plurality of correlation indices indicative of a level of correlation between the first engine and each one of the plurality of reference engines;
comparing the correlation indices to a threshold to determine a subset of the plurality of reference engines for which the threshold is exceeded;
obtaining performance history for the engines in the subset;
determining, from the performance history, that the first engine has a similarity in performance with the engines in the subset; and
generating, based on the similarity in performance, an output indicating a predicted performance for the first engine.

18. The computer readable medium of claim 17, wherein obtaining features of the plurality of particles extracted from the fluid sample comprises:
identifying a first set of particles of the fluid sample, each particle in the first set of particles having a chemical composition satisfying a chemical composition criteria; and
identifying a first profile of particles from the first set of particles, each particle in the first profile having a size and an aspect ratio satisfying a profile criteria.

19. The computer readable medium of claim 18, wherein obtaining features of particles of the plurality of reference fluid samples comprises:
for each one of the plurality of reference fluid samples:
identifying a reference set of particles of a respective reference fluid sample, each particle in the reference set of particles having a chemical composition satisfying the chemical composition criteria; and
identifying a reference profile of particles from the reference set of particles, each particle in the reference profile having a size and an aspect ratio satisfying a profile criteria.

20. The computer readable medium of claim 19, wherein determining the plurality of correlation indices comprises:
for each one of the plurality of reference fluid samples:
determining, using size and aspect ratio as axes of a two-dimensional coordinate system, a plurality of average distances between particles in each of the first profile and the reference profile and a respective center of each of the first profile and the reference profile; and
determining a correlation index based on the plurality of average distances.

* * * * *